United States Patent [19]

Petropoulos et al.

[11] 4,173,473

[45] Nov. 6, 1979

[54] RADIATION SENSITIVE COMPOSITIONS CONTAINING PYRYLIUM COMPOUNDS

[75] Inventors: Constantine C. Petropoulos, Webster; George A. Reynolds; James A. Van Allan, both of Rochester, all of N.Y.

[73] Assignee: Eastman Kodak Company, Rochester, N.Y.

[21] Appl. No.: 813,371

[22] Filed: Jul. 6, 1977

[51] Int. Cl.² ............................................. G03G 5/09
[52] U.S. Cl. ..................................... 430/72; 430/512; 430/517; 542/472; 252/300
[58] Field of Search ........................... 96/1.5, 1.6, 1 R

[56] References Cited

U.S. PATENT DOCUMENTS

| Re. 28,698 | 1/1976 | Murakami et al. | 96/1.6 |
| 3,250,615 | 5/1966 | Van Allan et al. | 96/1 R |
| 3,417,083 | 12/1968 | Reynolds et al. | 260/240 |
| 3,615,414 | 10/1971 | Light | 96/1.6 |
| 3,881,924 | 5/1975 | Murakami et al. | 96/1.6 |
| 3,938,994 | 2/1976 | Reynolds et al. | 96/1.6 |

Primary Examiner—Roland E. Martin, Jr.
Assistant Examiner—John L. Goodrow
Attorney, Agent, or Firm—Ronald P. Hilst

[57] ABSTRACT

Pyrylium, thiapyrylium and selenapyrylium salts and derivatives thereof having a trimethine linkage containing an aryl substituent attached to at least one carbon atom of the trimethine linkage are disclosed. Radiation sensitive compositions, e.g., photoconductive compositions, containing such materials are also disclosed.

4 Claims, No Drawings

RADIATION SENSITIVE COMPOSITIONS CONTAINING PYRYLIUM COMPOUNDS

FIELD OF THE INVENTION

This invention relates to new organic radiation sensitive compounds useful, for example, in photoconductive compositions.

BACKGROUND OF THE INVENTION

The process of xerography, as disclosed by Carlson in U.S. Pat. No. 2,297,691, employs an electrophotographic element comprising a support material bearing a coating of a normally insulating material whose electrical resistance varies with the amount of incident actinic radiation it receives during an imagewise exposure. The element, commonly termed a photoconductive element, is first given a uniform surface charge after a suitable period of dark adaptation. The element is then exposed to a pattern of actinic radiation which has the effect of differentially reducing the potential of the surface charge in accordance with the relative energy contained in various parts of the radiation pattern. The differential surface charge or electrostatic latent image remaining on the electrophotographic element is then made visible by contacting the surface with a suitable electroscopic marking material. Such marking material or toner, whether contained in an insulating liquid or on a dry carrier, can be deposited on the exposed surface in accordance with either the charge pattern or in the absence of charge pattern as desired. The deposited marking material can then be either permanently fixed to the surface of the sensitive element by known means such as heat, pressure, solvent vapor and the like or transferred to a second element to which it may similarly be fixed. Likewise, the electrostatic latent image can be transferred to a second element and developed there.

Various photoconductive insulating materials have been employed in the manufacture of electrophotographic elements. For example, vapors of selenium and vapors of selenium alloys deposited on a suitable support and particles of photoconductive zinc oxide held in a resinous, film-forming binder have found wide application in present-day document copying applications.

Since the introduction of electrophotography, a great many organic compounds have been found to possess some degree of photoconductivity. Many organic compounds such as poly(vinyl carbazole) have revealed a useful level of photoconduction and have been incorporated into photoconductive compositions. Optically clear organic photoconductor-containing elements having desirable electrophotographic properties can be especially useful in electrophotography. Such electrophotographic elements may be exposed through a transparent base, if desired, thereby providing unusual flexibility in equipment design. Such compositions when coated as a film or layer on a suitable support also yield an element which is reusable; that is, it can be used to form subsequent images after residual toner from prior images has been removed by transfer and/or cleaning.

Although many of the organic photoconductor materials are inherently light sensitive, their degree of sensitivity is usually low so that it is often necessary to add materials to increase their speed. Increasing the electrophotographic speed has several advantages in that it reduces exposure time, allows projection printing through various optical systems, etc. By increasing the speed through the use of sensitizers, photoconductors which would otherwise have been unsatisfactory are useful in processes where higher speeds are required. Accordingly, there is a need for new materials useful as sensitizers of organic photoconductor-containing systems.

Pyrylium salts, as disclosed in Davis et al, U.S. Pat. No. 3,141,770 issued July 21, 1964 and in VanAllan et al, U.S. Pat. No. 3,250,615 issued May 10, 1966, have been found to be useful sensitizing compounds for photoconductive compositions, especially organic photoconductive compositions. Since the initial discoveries of Davis et al and VanAllan et al as set forth in the above-referred to patents, a variety of new individual species of pyrylium salts, as well as thiapyrylium and selenapyrylium salts, have been discovered and found to be useful as radiation sensitive addenda in photoconductive compositions as well as in other radiation senstitive compositions such as laser Q-switches and various types of filter elements such as infrared absorbing filter elements. For example, Reynolds and VanAllan in U.S. Pat. No. 3,417,083 issued Dec. 17, 1968 disclose the use of certain new stable polymethine pyrylium and thiapyrylium salts useful as laser Q-switches and as infrared absorbing dyes useful in various filter applications. In addition to the various polymethine pyrylium and thiapyrylium dye structures shown in U.S. Pat. No. 3,417,083, Reynolds et al in U.S. Pat. No. 3,938,994 issued Feb. 17, 1976 discloses the use of certain monomethine pyrylium and thiapyrylium salts useful as sensitizers in an organic photoconductive composition.

Because of the especially useful properties which have been found to be associated with various pyrylium, thiapyrylium, and selenapyrylium salts, much work has been done pertaining to the synthesis of pyrylium salts to discover further new and useful species of these materials. In this regard, for background purposes, reference may be made to those species of pyrylium salts disclosed, for example, in Contois et al, U.S. Pat. No. 3,586,500 issued June 22, 1971 and in Contois U.S. Pat. No. 3,577,235 issued May 4, 1971. Still other species of pyrylium salts which have been found to be useful as sensitizers for low-color photoconductive compositions are disclosed in VanAllan, U.S. Pat. No. 3,554,745 issued Jan. 12, 1971. Still other species of pyrylium salt materials are disclosed in Defensive Publications Nos. T889,021; T889,022; and T889,023; all issued on Aug. 31, 1971. Yet other useful species of pyrylium salt materials are disclosed in Belgium Pat. No. 754,066 dated Sept. 30, 1970 and in Reynolds et al, U.S. patent application Ser. No. 60,634 filed Aug. 3, 1970 and now abandoned.

SUMMARY OF THE INVENTION

In accord with the present invention there are provided novel pyrylium, thiapyrylium, and selenapyrylium salts and derivatives thereof, hereinafter referred to as pyrylium-type salts, which contain a trimethine linkage having an aryl substituent bonded to at least one of the carbon atoms of the trimethine linkage. These materials and radiation sensitive compositions containing the same unexpectedly exhibit advantageous and superior properties when compared to closely related pyrylium-type salts absent such an aryl substituent in the trimethine linkage thereof.

For example, the novel pyrylium salts of the present invention, when incorporated in photoconductive compositions, have been found to unexpectedly yield substantially higher photosensitivity than closely related trimethine-containing pyrylium salts; and these same novel pyrylium salts have also been found to advantageously exhibit low visual coloration so that they are useful in radiation sensitive compositions wherein low color components are required, e.g., as sensitizers for use in (a) substantially colorless, transparent organic photoconductive compositions and (b) photoconductive coated paper elements wherein the resultant coated paper material is desired to have the color and appearance of plain paper (bond paper).

In addition, the novel salts of the present invention exhibit light absorption properties extending into the infrared portion of the spectrum so that these compositions may be used in a variety of different radiation sensitive elements requiring infrared absorbing, radiation sensitive addenda.

DESCRIPTION OF THE PREFERRED EMBODIMENTS

Representative pyrylium-type salts of our invention have, or represent an equivalent of a material having, a structure of the following formula:

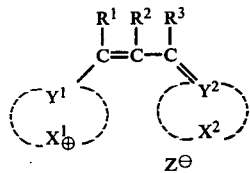

wherein:
- each of $X^1$ and $X^2$, which may be the same or different, represent oxygen, sulfur, or selenium;
- each of $Y^1$ and $Y^2$, which may be the same or different, represent the atoms necessary to complete a substituted or unsubstituted heterocyclic unsaturated ring nucleus having 6 or 10 ring atoms including a selenium, sulfur or oxygen hetero ring atom and 5 or 9 carbon ring atoms;
- each of $R^1$, $R^2$, and $R^3$, which may be the same or different, represent hydrogen, halogen such as chlorine or bromine, cyano, nitro, substituted or unsubstituted alkyl having 1 to about 4 carbon atoms in the alkyl group, or substituted or unsubstituted aryl, e.g., phenyl and alkoxyphenyl, with the proviso that at least one of $R^1$, $R^2$, or $R^3$ represents substituted or unsubstituted aryl; and
- $Z^\ominus$ represents an anionic function such as a perchlorate, fluoroborate, or hexafluoroborate anion.

A partial listing of representative substituent groups which may be present in the case where any one of $R^1$–$R^3$ represents a substituted aryl includes alkyl and alkoxy groups having 1 to about 4 carbon atoms; amino groups including alkyl- and phenyl-substituted amino groups such as dialkylaminos wherein the alkyl substituents of such amino groups contain 1 to about 4 carbon atoms, dibenzylaminos, diphenylaminos, ditolylaminos; and equivalent aryl substituents.

A partial listing of representative substituent groups which may be present in the case where any one of $R^1$–$R^3$ represents a substituted alkyl includes phenyl groups, alkoxy and amino groups as defined above, and equivalent alkyl substituents.

In accord with certain preferred embodiments of the invention, each of $R^1$–$R^3$ in Formula I, which may be the same or different, represent hydrogen, alkyl having 1 to 4 carbon atoms, phenyl or alkoxyphenyl, at least one of $R^1$–$R^3$ being phenyl or alkoxyphenyl; and the heterocyclic rings containing $Y^1$ in formula I above represent groups having either of formulas II or III and the heterocyclic rings containing $Y^2$ in formula I represent groups having either of formulas IV or V:

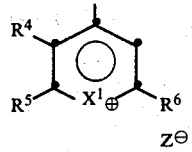

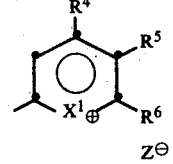

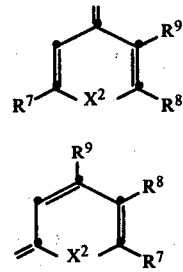

wherein:
- each of $X^1$ and $X^2$, which may be the same or different, represent oxygen or sulfur;
- Z is as defined above; and
- each of $R^4$, $R^5$, $R^6$, $R^7$, $R^8$, and $R^9$, which may be the same or different, represent hydrogen; alkyl having 1 to about 4 carbon atoms in the alkyl group, including alkyls substituted with an alkoxy having 1 to about 4 carbon atoms, an amino substituent of the type defined hereinabove with respect to $R^1$–$R^3$, or phenyl; substituted or unsubstituted aryl as defined hereinabove with respect to $R^1$–$R^3$; and when taken together any two $R^4$–$R^9$ groups attached to adjacent carbon ring atoms represent the atoms necessary to complete substituted or unsubstituted aryl as defined hereinabove with respect to $R^1$–$R^3$.

Although the heterocyclic structures of formulas II–V above presently represent preferred embodiments of the pyrylium-type salts of the invention, it should be understood that a variety of equivalent structures are also contemplated within the scope of the present invention. Among the various references to which one may refer for further information regarding such heterocyclic structures are the various United States patents and Defensive Publications referred to in the "Background of the Invention." It is to be understood that of primary importance in the present invention is the presence of the aromatic substituent on the trimethine linkage.

The pyrylium salts described herein can be prepared by one of the general reaction sequences described hereinafter. The thiapyrylium and selenapyrylium analogs of these salts can be prepared by similar techniques, except that in these cases the hetero oxygen atom appearing in the pyrylium or flavylium salt starting materials are replaced by a sulfur or selenium hetero atom, respectively. According to one general reaction scheme, symmetrical salts are conveniently prepared as follows:

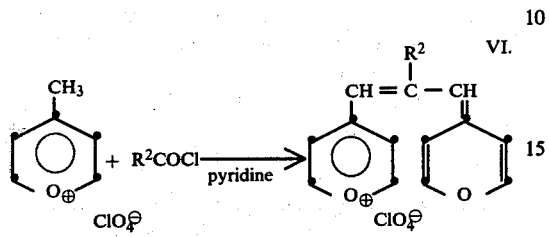

wherein $R^2$ is as defined hereinbefore.

Various substituted pyrylium salts bearing substituents represented by groups $R^4$–$R^6$ and $R^7$–$R^9$ in formulas II–V above can be prepared in accord with reaction scheme VI by utilizing appropriately substituted starting materials. For example, symmetrical pyranylidene salts are conveniently prepared from either 2 or 4-methylflavylium salts as illustrated in reaction scheme VII:

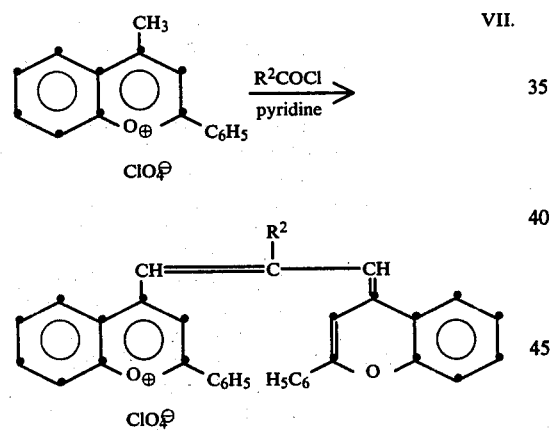

wherein $R^2$ is as defined hereinbefore.

Unsymmetrical pyrylium salts can be prepared by the condensation of a 4-arylacylidenepyran with a 2- or 4-methylflavylium salt or with a 2- or 4-methyl substituted pyrylium salt in the presence of acetic anhydride as illustrated in reaction schemes VIII and IX respectively.

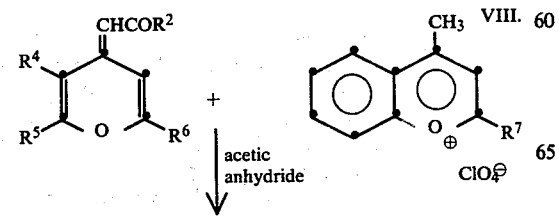

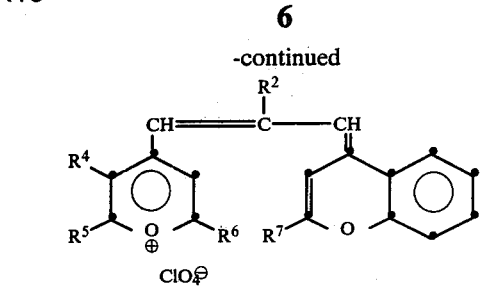

wherein $R^2$ and $R^4$–$R^7$, are as defined hereinbefore.

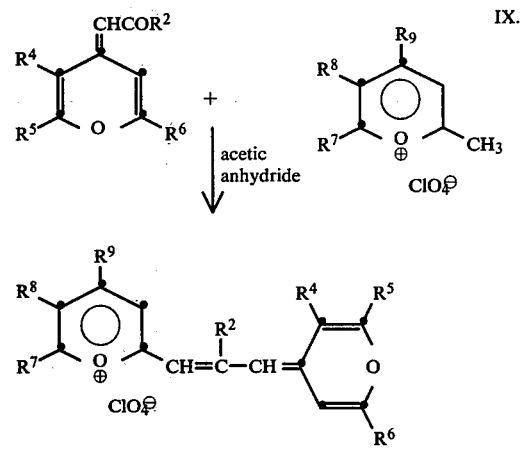

wherein $R^2$, $R^4$–$R^6$, and $R^7$–$R^9$ are as defined hereinbefore.

Where it is desired to prepare pyrylium salts of the present invention having substituents on the $\alpha$ or $\gamma$ position of the trimethine linkage, rather than the $\beta$ position of the linkage as illustrated in reaction schemes VI–IX above, this can be accomplished by reacting a formylmethylenepyran derivative and a 4-alkylpyrylium in refluxing 1,2,3-trichloropropane as illustrated in reaction scheme X:

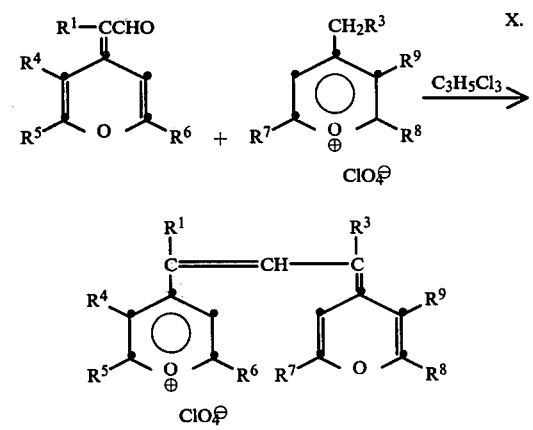

wherein $R^1$, $R^3$, $R^4$–$R^6$, and $R^7$–$R^9$ are as defined hereinbefore.

Photoconductive compositions and electrophotographic elements containing the same can be prepared with a variety of organic and inorganic photoconductive materials together with the pyrylium-type salts described herein. Typically, in such photoconductive compositions the pyrylium-type salts described herein are present as sensitizers. Such photoconductive compositions can be prepared by blending a dispersion or solution of the photoconductive compound together with an electrically insulating, film-forming resin binder when necessary or desirable and coating or forming a self-supporting layer with the photoconductive composition. Generally, a suitable amount of the sensitizing compound is mixed with the photoconductive coating composition so that after thorough mixing, the sensitizing compound is uniformly distributed throughout the desired layer of the coated element. The amount of sensitizer that can be added to a photoconductor-containing layer to give effective increases in speed can vary widely. The optimum concentration in any given case will vary with the specific photoconductor and sensitizing compound used.

In general, an appropriate sensitizer is added in a concentration range from about 0.0001 to about 30 percent by weight based on the dry weight of the film-forming coating composition. Normally, the sensitizer is added to the coating composition in an amount from about 0.005 to about 10 percent by weight of the total coating composition.

The sensitizers used in this invention are effective for enhancing the electrophotosensitivity of a wide variety of organic and inorganic photoconductors, particularly organic, including organo-metallic photoconductors. A partial listing of representative organic photoconductors useful in photosensitive compositions containing the present sensitizers is set forth below.

1. Arylamine photoconductors including substituted and unsubstituted arylamines, diarylamines, nonpolymeric triarylamines and polymeric triarylamine such as those described in Fox, U.S. Pat. No. 3,240,597, issued Mar. 15, 1966 and Klupfel et al., U.S. Pat. No. 3,180,730, issued Apr. 27, 1965;

2. Polyarylalkane photoconductors of the types described in Noe et al. U.S. Pat. No. 3,274,000, issued Sept. 20, 1966, Wilson U.S. Pat. No. 3,542,547, issued Nov. 24, 1970 and in Seus et al., U.S. Pat. No. 3,542,544, issued Nov. 24, 1970;

3. 4-Diarylamino-substituted chalcones of the types described in Fox U.S. Pat. No. 3,526,501, issued Sept. 1, 1970;

4. Non-ionic cycloheptenyl compounds of the types described in Looker U.S. Pat. No. 3,533,786, issued Oct. 13, 1970;

5. Compounds containing an

nucleus, as described in Fox U.S. Pat. No. 3,542,546, issued Nov. 24, 1970;

6. Organic compounds having a 3,3'-bis-aryl-2-pyrazoline nucleus, as described in Fox et al. U.S. Pat. No. 3,527,602, issued Sept. 8, 1970;

7. Triarylamines in which at least one of the aryl radicals is substituted by either a vinyl radical or a vinylene radical having at least one active hydrogen-containing group, as described in Brantly et al. U.S. Pat. No. 3,567,450, issued Mar. 2, 1971;

8. Triarylamines in which at least one of the aryl radicals is substituted by an active hydrogen-containing group, as described in Brantly et al. Belgian Pat. No. 728,563, dated Apr. 30, 1969;

9. Any other organic compound which exhibits photoconductive properties such as those set forth in Australian Pat. No. 248,402 and the various polymeric photoconductors such as the photoconductive carbazol polymers described in U.S. Pat. No. 3,421,891, dated Jan. 14, 1969.

Preferred binders for use in preparing the photoconductive layers which can be sensitized in accordance with the method of this invention comprise polymers having fairly high dielectric strength which are good electrically insulating film-forming vehicles. Materials of this type comprise styrene-butadiene copolymers; silicone resins; styrene-alkyd resins; silicone alkyd resins; soya-alkyd resins; poly(vinyl chloride); poly(vinylidene chloride); vinylidene chloride-acrylonitrile copolymers; poly(vinyl acetate); vinyl acetate-vinyl chloride copolymers; poly(vinyl acetals), such as poly(vinyl butyral); polyacrylic and methacrylic esters, such as poly(methylmethacrylate), poly(n-butylmethacrylate), poly(isobutyl methacrylate); etc.; polystyrene; nitrated polystyrene; polymethylstyrene; isobutylene polymers; polyesters, such as poly(ethylene alkaryloxyalkylene terephthalate); phenolformaldehyde resins; ketone resins; polyamides; polycarbonates; polythiocarbonates; poly(ethyleneglycol-co-bishydroxyethoxyphenylpropane terephthalate); nuclear substituted polyvinyl haloarylates; etc. Methods of making resins of this type have been described in the prior art, for example, styrene-alkyd resins can be prepared according to the method described in U.S. Pat. Nos. 2,361,019 and 2,258,423. Suitable resins of the type contemplated for use in the photoconductive layers of the invention are sold under such tradenames or trademarks as Vitel ® PE-101, Cymac, Piccopale 100, Saran F-220 and Lexan ® 105 and 145. Other types of binders which can be used in the photoconductive layers of the invention include such materials as paraffin, mineral waxes, etc. If a polymeric photoconductor is used, the binder may be omitted altogether.

The organic coating solvents useful for preparing the above coating dopes can be selected from a variety of materials. Useful liquids are hydrocarbon solvents, including substituted hydrocarbon solvents, with preferred materials being halogenated hydrocarbon solvents. The requisite properties of the solvent are that it be capable of dissolving the pyrylium dye and capable of dissolving or at least highly swelling or solubilizing the polymeric ingredient of the composition. In addition, it is helpful if the solvent is volatile, preferably having a boiling point of less than about 200° C. Particularly useful solvents include halogenated lower alkanes having from 1 to about 3 carbon atoms, such as dichloromethane, dichloroethane, dichloropropane, trichloromethane, trichloroethane, tribromomethane, trichloromonofluoromethane, trichlorotrifluoroethane, etc.; aromatic hydrocarbons such as benzene, toluene as well as halogenated benzene compounds such as chlorobenzene, bromobenzene, dichlorobenzene, etc.; ketones such as dialkyl ketones having 1 to about 3 carbon atoms in the alkyl moiety such as dimethylketone, methylethylketone, etc.; and ethers such as tetrahydrofuran, etc. Mixtures of these and other solvents can also be used.

In preparing the photoconductive coating composition, useful results are obtained where the photoconductor substance is present in an amount equal to at least about 1 weight percent based on the dry weight of the coating composition. The upper limit in the amount of photoconductor substance present can be widely varied in accordance with usual practice. In those cases where a binder is employed, it is normally required that the photoconductor substance be present in an amount from about 1 weight percent of the coating composition to about 99 weight percent of the coating composition. A polymeric photoconductor can be employed in which case an additional binder may not be required. A preferred weight range for the photoconductor substance in the coating composition is from about 10 weight percent to about 60 weight percent.

Suitable supporting materials for coating photoconductive layers which can be sensitized in accordance with the method of this invention can include any of a wide variety of electrically conducting supports, for example, paper (at a relative humidity above 20 percent); aluminum-paper laminates; metal foils such as aluminum foil, zinc foil, etc.; metal plates, such as aluminum, copper, zinc, brass and galvanized plates; vapor deposited metal layers such as silver, nickel, aluminum and the like coated on paper or conventional photographic film bases such as cellulose acetate, polystyrene, etc. Such conducting materials as nickel can be vacuum deposited on transparent film supports in sufficiently thin layers to allow electrophotographic elements prepared therewith to be exposed from either side of such elements. An especially useful conducting support can be prepared by coating a support material such as poly(ethylene terephthalate) with a conducting layer containing a semiconductor dispersed in a resin. Such conducting layers both with and without insulating barrier layers are described in U.S. Pat. No. 3,245,833. Likewise, a suitable conducting coating can be prepared from the sodium salt of a carboxyester lactone of maleic anhydride and a vinyl acetate polymer. Such kinds of conducting layers and methods for their optimum preparation and use are disclosed in U.S. Pat. Nos. 3,007,901 and 3,262,807.

Coating thicknesses of the photoconductive composition on the support can vary widely. Normally, a coating in the range of about 10 microns to about 300 microns before drying is useful for the practice of this invention. The preferred range of coating thickness is found to be in the range from about 50 microns to about 150 microns before drying, although useful results can be obtained outside of this range. The resultant dry thickness of the coating is preferably between about 1 micron and about 50 microns, although useful results can be obtained with a dry coating thickness between about 0.5 and about 200 microns.

The elements of the present invention can be employed in any of the well-known electrophotographic processes which require photoconductive layers. One such process is the xerographic process as described, for example, in the "Background of the Invention" set forth herein and in U.S. Pat. No. 3,938,994 referred to hereinbefore.

As indicated earlier herein, the pyrylium-type salts of the invention can be useful as a radiation sensitive material in a variety of radiation sensitive compositions and elements. One preferred embodiment of such radiation sensitive compositions is illustrated by the photoconductive compositions described hereinbefore. However, the pyrylium-type salts of the invention can also be used in radiation sensitive elements other than the aforementioned photoconductor elements. In this connection, the pyrylium-type salts of the invention are regarded as particularly useful radiation sensitive addenda because of their advantageous properties of low visible coloration combined with good transmittance of visible light radiation and unusually high absorptivity and sensitivity to radiation in the far red and near infrared portions of the electromagnetic spectrum, herein defined as radiation having a wavelength greater than about 680 nm. For example, the pyrylium-type salts of the invention can be incorporated in various thermographic compositions and elements as a radiation sensitive material sensitive to infrared or heat radiation. In such applications, the radiation sensitive pyrylium-type salts of the invention can be applied as a layer to a support, preferably together with a carrier material for the salt, such as a binder, and other necessary or desireable radiation sensitive or image-forming materials.

In addition, the pyrylium-type salts of the invention can be used as a radiation sensitive filter composition and element to filter out or remove undesired infrared radiation. In such case, a simple layer containing the pyrylium-type salts of the invention (and optionally a binder) or a solution or dispersion of the pyrylium-type salt in a liquid carrier can be employed as an effective radiation sensitive filter composition or element in accord with the invention.

As will be appreciated, the various carrier materials such as binders and liquids optionally employed in radiation sensitive compositions together with the pyrylium-type salts of the invention can be selected from among a wide variety of materials which do not substantially impair the radiation sensitivity and absorption properties of the pyrylium-type salts of the invention, i.e., the carrier material is a "non-interfering" carrier. A partial listing of useful such carriers would include any of the electrically insulating binders described for use hereinbefore in photoconductive compositions as well as many conventional photographic silver halide vehicles including various colloid materials containing gelatin, gelatin derivatives or a variety of other hydrophilic naturally-occurring and synthetic substances such as those described in Product Licensing Index, Vol. 92, December, 1971, publication 9232, page 108, paragraph VIII. (The publication Product Licensing Index is published by Industrial Opportunities Ltd., Homewell, Havant, Hampshire, P09 1ET, United Kingdom.)

The following examples are included for a further understanding of the invention.

EXAMPLE 1

Preparation of 4-[3-(2,6-Diphenyl-4H-pyran-4-ylidene)-2-phenylpropen-1-yl]-2,6-diphenylpyrylium perchlorate having the formula:

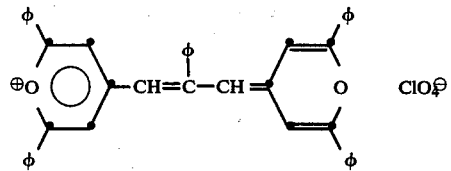

where $\phi$ represents —$C_6H_5$, i.e., a phenyl group.

A mixture of 5 g. of 4-methyl-2,6-diphenylpyrylium perchlorate, 10 ml. of acetonitrile, 10 ml. of benzoyl chloride and 5 ml. of pyridine was refluxed for 5 minutes, cooled and the solid was collected and extracted in a Soxhlet extractor with acetonitrile. The resultant product was identified as the above-noted pyrylium salt having a melting point of 303°–304° C. and an empirical formula of $C_{43}H_{31}ClO_6$.

EXAMPLE 2

Preparation of 4-[3-(2,6-Diphenyl-4H-pyran-4-ylidene)-2-phenylpropen-1-yl]flavylium perchlorate having the formula:

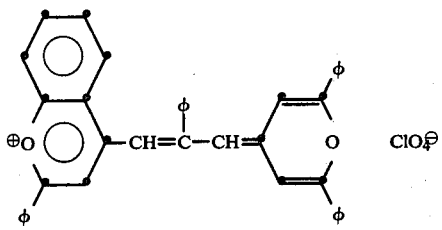

A mixture of 1 g. 2,6-diphenyl-4-phenacylidene-4H-pyran, 1.3 g. of 4-methylflavylium perchlorate and 20 ml. of acetic anhydride was refluxed for 15 minutes, chilled and the solid was collected and purified by extraction. The resultant product had a melting point of 299°–300° C. and was identified as the above-noted pyrylium salt having an empirical formula of $C_{41}H_{29}ClO_6$.

EXAMPLE 3

Preparation of 4-[3-(4H-Benzopyran-4-ylidene)-2-phenylpropen-1-yl]flavylium perchlorate having the formula:

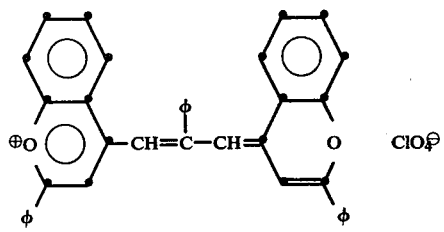

This pyrylium salt was made in a manner identical to that set forth in Example 1 above, except the pyrylium perchlorate salt starting material of Example 1 was replaced with 4-methylflavylium perchlorate. The pyrylium salt product was identified as the above-noted salt having a melting point of 298°–299° C. and an empirical formula of $C_{39}H_{27}ClO_6$.

EXAMPLE 4

Preparation of 4-[3-(2,6-Diphenyl-4H-pyran-4-ylidene)-2-(p-methoxyphenyl)propen-1-yl]-2,6-diphenylpyrylium perchlorate having the formula:

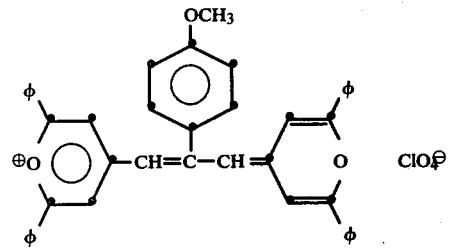

This pyrylium salt was prepared in a manner identical to that set forth in Example 1 above, except that benzoyl chloride used in Example 1 was replaced by p-anisoyl chloride. The resultant product was identified as the above-noted pyrylium salt having a m.p. of 312°–313° C. and an empirical formula of $C_{44}H_{33}ClO_7$.

EXAMPLE 5

The electronic absorption spectra of each of the four pyrylium salts prepared in Examples 1–4 was measured in methylene chloride using a Cary 14 spectrometer. The long wavelength absorption band, b, for each of these salts was as follows:

|  | b |
| --- | --- |
| Pyrylium salt of Example 1 | 690 nm. |
| Pyrylium salt of Example 2 | 704 nm. |
| Pyrylium salt of Example 3 | 728 nm. |
| Pyrylium salt of Example 4 | 693 nm. |

EXAMPLE 6

A series of photoconductive compositions containing one of the following photoconductors:

A. triphenylamine
B. 4,4'-bis(diethylamino)-2,2'-dimethyltriphenylmethane
C. 4,4'-bis(diphenylamino)chalcone as the photoconductive material was prepared for coating on a conducting support material by mixing 0.25 part of the photoconductor with 0.01 part by weight of one of the following compounds:

1. 4-[3-(2,6-Diphenyl-4H-pyran-4-ylidene)-2-phenylpropen-1-yl]-2,6-diphenylpyrylium perchlorate
2. 4-[3-(2,6-Diphenyl-4H-pyran-4-ylidene)-2-phenylpropen-1-yl]flavylium perchlorate
3. 4-[3-(4H-Benzopyran-4-ylidene)-2-phenylpropen-1-yl]flavylium perchlorate
4. 4-[3-(2,6-Diphenyl-4H-pyran-4-ylidene)-2-(p-methoxyphenyl)propen-1-yl]-2,6-diphenylpyrylium perchlorate as sensitizer and dissolving the mixture, together with 1.0 part by weight of a resinous polyester binder, by stirring the mix into dichloromethane. The resultant mixture was then hand coated over a polymeric carboxy ester lactone layer carried on a transparent support. In all instances, the polyester binder in the coating composition was Vitel PE-101 (trademark of Goodyear Tire and Rubber Co.), believed to be poly(4,4'-isopropylidenebisphenoxyethylene-co-ethylene terephthalate) 50/50. The wet coating thickness of the support was 0.01 cm. After drying, a sample of each electrophotographic element was employed in a standard electrophotographic process which includes charging under a positive corona discharge until the surface potential of the sample, as measured by an electrometer probe, reached 600 volts. Similarly, the sample of each element was charged under a negative source until the surface potential reached 600 volts. Each of the samples was then exposed from behind a transparent stepped density gray scale to a 3000° K. tungsten source of 20 foot-candle illuminance at the point of exposure. The exposure caused reduction of surface potential of the element under each step of the gray scale from its initial potential, $V_o$, to some lower potential, V, the exact value of which depends upon the actual amount of exposure received by each area. The results of these measurements were then plotted on a graph of surface potential V versus log exposure for each step. The actual speed of each element was expressed in terms of the reciprocal of the exposure required to reduce the surface potential to any fixed arbitrarily assigned value. Numerically, the shoulder speeds noted below are the quotient of $10^4$ divided by the exposure in meter candle seconds required to reduce the potential by 100 volts. The toe speeds noted below are the quotient of $10^4$ divided by the exposure in meter-candle-seconds required to reduce the initial voltage, $V_o$, to an absolute value of 100 volts. The results of these speed measurements are given in the following table.

TABLE I

| Compound Number | Organic Photoconductor | Speed | | | |
|---|---|---|---|---|---|
| | | Positive | | Negative | |
| | | Shoulder | Toe | Shoulder | Toe |
| 1 | A | 900 | 50 | 630 | 25 |
| 2 | A | 900 | 57 | 900 | 32 |
| | B | 1000 | 63 | 1200 | 40 |
| | C | 1600 | 80 | 1000 | 45 |
| 3 | A | 1200 | 50 | 800 | 25 |
| | B | 1000 | 57 | 900 | 29 |
| | C | 900 | 57 | 450 | 40 |
| 4 | A | 1200 | 45 | 1000 | 18 |
| | B | 1200 | 63 | 1600 | 32 |
| | C | 1400 | 63 | 1000 | 25 |

For comparison, photoconductors A, B and C employed in the photoconductive compositions used to obtain the data shown in Table I are evaluated in samples containing no sensitizer. The speeds are as follows:

TABLE II

| Organic Photoconductor | Speed | | | |
|---|---|---|---|---|
| | Positive | | Negative | |
| | Shoulder | Toe | Shoulder | Toe |
| A | 44 | 0 | 52 | 0 |
| B | 19 | 0 | 18 | 0 |
| C | 101 | 0 | 32 | 0 |

As an additional basis for comparison, pyrylium salts having a trimethine linkage and which are otherwise structurally similar to compounds 1-4 above, except that they do not possess an aryl substituent attached to a carbon atom of the methine linkage, were evaluated as sensitizers with photoconductors A, B, and C noted above. These evaluations were carried out by preparing photoconductive compositions and making speed measurements on the resultant photoconductive compositions in a manner identical to that described above. The resulting speed values obtained are set forth in Table III as follows:

TABLE III

| Pyrylium Salt Compound Tested[1] | Organic Photoconductor | Speed | | | |
|---|---|---|---|---|---|
| | | Positive | | Negative | |
| | | Shoulder | Toe | Shoulder | Toe |
| i | A | 29 | 0 | 20 | 0 |
| | B | 220 | 10 | 140 | 9 |
| ii | A | 32 | 0 | 40 | 0 |
| | B | 570 | 29 | 450 | 25 |
| | C | 120 | 12 | 110 | 9 |
| iii | A | 36 | 0 | 36 | 0 |
| | B | 100 | 4.5 | 100 | 4.0 |
| | C | 63 | 0 | 70 | 5.0 |
| iv | A | 100 | 3.2 | 71 | 2.5 |
| | B | 160 | 5.0 | 120 | 4.0 |
| | C | 160 | 8.0 | 120 | 5.0 |
| v | A | 52 | 3.5 | 80 | 3.0 |
| | B | 280 | 13 | 500 | 12 |
| | C | 130 | 3.0 | 63 | — |
| vi | A | 120 | 0 | 250 | 0 |
| | B | 200 | 5.6 | 58 | 6.3 |
| | C | 120 | 0 | 120 | 0 |
| vii | A | 50 | 0 | 32 | 0 |
| | B | 250 | 18 | 360 | 11 |
| | C | 70 | 3.6 | 90 | 0 |
| viii | A | 200 | 16 | 180 | 6.3 |
| | B | 400 | 32 | 250 | 18 |

TABLE III-continued

| Pyrylium Salt Compound Tested[1] | Organic Photo-conductor | Speed | | | |
|---|---|---|---|---|---|
| | | Positive | | Negative | |
| | | Shoulder | Toe | Shoulder | Toe |
| | C | 630 | 55 | 400 | 25 |

[1]Compound i has the chemical name 4-[1,3-dimethyl-3-(2,6-diphenyl-4H-pyran-4-ylidene)propen-1-yl]-2,6-diphenylpyrylium perchlorate and the following structural formula:

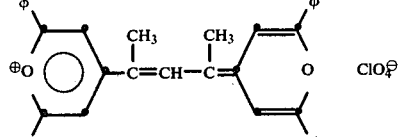

Compound ii has the chemical name 4-[2-methyl-3-(2,6-diphenyl-4H-pyran-4-ylidene)propen-1-yl]-2,6-diphenylpyrylium perchlorate and the following structural formula:

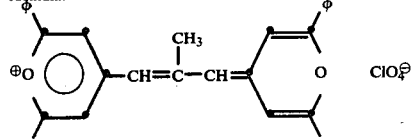

Compound iii has the chemical 4-[3-(4H-benzopyran-4-ylidene)-2-ethylpropen-1-yl]flavylium perchlorate and the following structural formula:

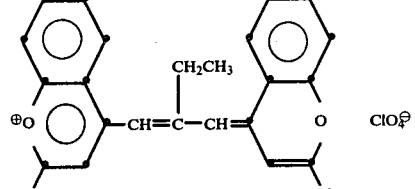

Compound iv has the chemical name 4-[2-ethyl-3-(2,6-diphenyl-4H-pyran-4-ylidene)propen-1-yl]-2,6-diphenylpyrylium perchlorate and the following structural formula:

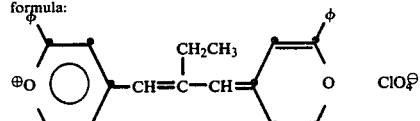

Compound v has the chemical name 4-[3-(2,6-diphenyl-4H-pyran-4-ylidene)propen-1-yl]-2,6-diphenylpyrylium perchlorate and the following structural formula:

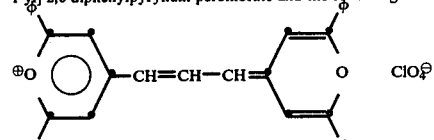

Compound vi has the chemical name 4-[3-(4H-benzopyran-4-ylidene)-2-methylpropen-1-yl]flavylium perchlorate and the following structural formula:

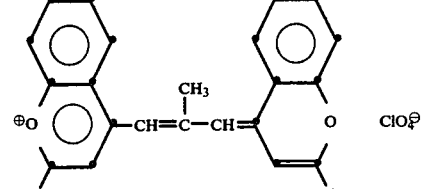

Compound vii has the chemical name 4-[3-methyl-3-(2,6-diphenyl-4H-pyran-4-ylidene)propen-1-yl]-2,6-diphenylpyrylium perchlorate and the following structural formula:

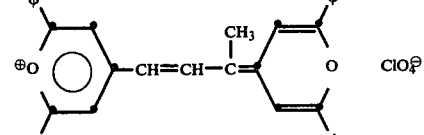

Compound viii has the chemical name 2,6-di-t-butyl-4-[3-2,6-di-t-butyl-4H-pyran-4-ylidene)propen-1-yl]pyrylium perchlorate and the following structural formula:

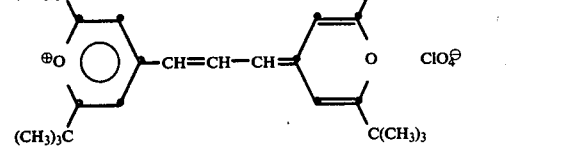

As can be seen by comparing Table I to Table III, the pyrylium salts of the present invention which have a trimethine linkage bearing an aryl substituent can be used in photoconductive compositions to impart thereto significantly higher speeds, i.e., light sensitivity, than can be imparted to identical compositions using structurally similar pyrylium salts, except that these latter salts do not possess an aryl substituent on the trimethine linkage thereof.

The invention has been described in detail with particular reference to certain preferred embodiments thereof, but it will be understood that variations and modifications can be effected within the spirit and scope of the invention.

We claim:

1. A photoconductive composition comprising an electrically insulating material containing a sensitizing amount of a pyrylium-type salt having the formula:

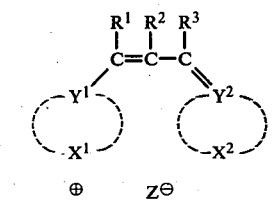

wherein:
each of $X^1$ and $X^2$, which may be the same or different, represents oxygen, sulfur, or selenium;
each of $Y^1$ and $Y^2$, which may be the same or different, represents the atoms necessary to complete a heterocyclic unsaturated ring nucleus having 6 or 10 ring atoms including a selenium, sulfur or oxygen hetero ring atom and 5 or 9 carbon ring atoms;
each of $R^1$, $R^2$, and $R^3$, which may be the same or different, represents hydrogen, halogen, cyano, nitro, alkyl having 1 to about 4 carbon atoms in the alkyl group, or aryl, with the proviso that at least one of $R^1$, $R^2$, or $R^3$ represents aryl; and
$Z^{\ominus}$ represents an anionic function.

2. A photoconductive composition as defined in claim 1 wherein:
each of $R^1$-$R^3$, which may be the same or different, represents hydrogen, alkyl, phenyl or alkoxyphenyl;
the heterocyclic ring containing $Y^1$ represents a group having one of the following structures:

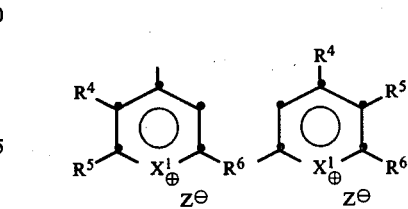

and wherein the heterocyclic ring containing $Y^2$ represents a group having one of the following structures:

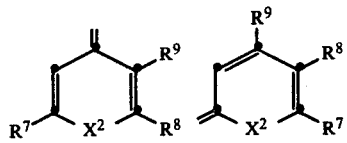

wherein each of $X^1$ and $X^2$, which may be the same or different, represents oxygen or sulfur;

Z represents an anionic function; and each of $R^4$, $R^5$, $R^6$, $R^7$, $R^8$, and $R^9$, which may be the same or different, represents hydrogen, alkyl having 1 to 4 carbon atoms in the alkyl group, phenyl, and when taken together any two $R^4$–$R^9$ groups attached to adjacent carbon ring atoms represent the atoms necessary to complete an aryl ring.

3. A photoconductive composition as defined in claim 1 wherein said pyrylium-type salt is selected from the group consisting of 4-[3-(2,6-Diphenyl-4H-pyran-4-ylidene)-2-phenylpropen-1-yl]-2,6-diphenylpyrylium perchlorate; 4-[3-(2,6-Diphenyl-4H-pyran-4-ylidene)-2-phenylpropen-1-yl]flavylium perchlorate; 4-[3-(4H-Benzopyran-4-ylidene)-2-phenylpropen-1-yl]flavylium perchlorate; and 4-[3-(2,6-Diphenyl-4H-pyran-4-ylidene)-2-(p-methoxyphenyl)propen-1-yl]-2,6-diphenylpyrylium perchlorate.

4. A photoconductive composition comprising an electrically insulating material containing an organic photoconductor and a sensitizing amount of pyrylium-type salt having the formula:

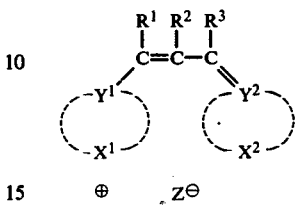

wherein each of $X^1$ and $X^2$, which may be the same or different, represents oxygen, sulfur, or selenium;

each of $Y^1$ and $Y^2$, which may be the same or different, represents the atoms necessary to complete a heterocyclic unsaturated ring nucleus having 6 or 10 ring atoms including a selenium, sulfur or oxygen hetero ring atom and 5 or 9 carbon ring atoms;

each of $R^1$, $R^2$, and $R^3$, which may be the same or different, represents hydrogen, halogen, cyano, nitro, alkyl having 1 to about 4 carbon atoms in the alkyl group, or aryl, with the proviso that at least one of $R^1$, $R^2$, or $R^3$ represents aryl; and $Z^\ominus$ represents an anionic function.

* * * * *